(12) United States Patent
Alberte, Jr. et al.

(10) Patent No.: US 8,203,447 B2
(45) Date of Patent: Jun. 19, 2012

(54) TELEMETRY SYSTEM AND METHOD

(75) Inventors: Robert Joseph Alberte, Jr., Oconomowoc, WI (US); Bruce Arnold Friedman, Jasper, GA (US); Mathew George Grubis, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 438 days.

(21) Appl. No.: 12/397,710

(22) Filed: Mar. 4, 2009

(65) Prior Publication Data

US 2010/0225481 A1    Sep. 9, 2010

(51) Int. Cl.
*G08B 1/08* (2006.01)
(52) U.S. Cl. ................................. 340/539.12
(58) Field of Classification Search .............. 340/539.13, 340/539.23, 573.1, 573.4, 506
See application file for complete search history.

(56) References Cited

U.S. PATENT DOCUMENTS

| | | | | |
|---|---|---|---|---|
| 4,275,385 | A * | 6/1981 | White | 340/8.1 |
| 5,396,224 | A | 3/1995 | Dukes et al. | |
| 6,510,344 | B1 | 1/2003 | Halpern | |
| 7,242,306 | B2 * | 7/2007 | Wildman et al. | 340/573.1 |
| 7,248,933 | B2 * | 7/2007 | Wildman | 700/90 |
| 7,277,714 | B1 | 10/2007 | Mikan et al. | |
| 7,321,862 | B2 | 1/2008 | Rosenfeld et al. | |
| 7,429,243 | B2 | 9/2008 | KenKnight et al. | |
| 2002/0060630 | A1 * | 5/2002 | Power | 340/573.1 |
| 2003/0146835 | A1 | 8/2003 | Carter | |
| 2005/0035862 | A1 * | 2/2005 | Wildman et al. | 340/573.1 |
| 2006/0176149 | A1 | 8/2006 | Douglas | |
| 2006/0206011 | A1 * | 9/2006 | Higgins et al. | 600/300 |
| 2006/0226974 | A1 | 10/2006 | Fluegel | |
| 2006/0250234 | A1 * | 11/2006 | Maschke | 340/539.13 |
| 2007/0080801 | A1 * | 4/2007 | Weismiller et al. | 340/539.13 |
| 2007/0096897 | A1 | 5/2007 | Weiner | |
| 2008/0048914 | A1 | 2/2008 | Smith et al. | |
| 2008/0094208 | A1 | 4/2008 | Schwartz | |
| 2008/0275307 | A1 | 11/2008 | Poschmann | |
| 2009/0273455 | A1 * | 11/2009 | Sweeney et al. | 340/286.07 |

FOREIGN PATENT DOCUMENTS

WO    20070069890    6/2007

OTHER PUBLICATIONS

Zhu, Chen and Zhang, "The Principle of Non-Sensor Dead Reckoning," Geoscience and Remote Sensing Symposium, (Jul. 25, 2005) pp. 4693-4696.
Leonhardi, Nicu and Rothermel, "A Map-Based Dead Reckoning Protocol for Updating Location Information," Proceedings of International Parallel and Distributed Processing Symposium, 2002, pp. 193-200.

* cited by examiner

*Primary Examiner* — Phung Nguyen
(74) *Attorney, Agent, or Firm* — Andrus, Sceales, Starke & Sawall, LLP

(57) ABSTRACT

A telemetry system is disclosed herein. The telemetry system includes a transmitter configured to provide tracking data, and a receiver adapted to define a coverage area. The receiver is configured to receive the tracking data from the transmitter only when the transmitter is within the coverage area. The telemetry system also includes a processor configured to receive the tracking data from the receiver. The processor is configured to estimate the location of the transmitter when the transmitter is outside the coverage area based on the tracking data.

19 Claims, 3 Drawing Sheets

TELEMETRY SYSTEM AND METHOD

FIELD OF THE INVENTION

This disclosure relates generally to a telemetry system and method.

BACKGROUND OF THE INVENTION

Telemetry systems can be implemented to acquire and transmit data from a remote source. The telemetry system may incorporate a wireless technology such as wireless fidelity (WiFi); infrared (IR); or ultrasound in order to facilitate finding an object and/or data transmission. As an exemplary implementation, a medical telemetry system can be implemented to remotely monitor the cardiac electrical activity of a plurality of ambulatory patients while they remain within a predefined coverage area. The medical telemetry system may also be implemented locate and track patients within the coverage area.

The coverage area is often relatively small due to financial considerations associated with the requisite infrastructure. Accordingly, the coverage area typically does not cover the entire hospital interior, and does not extend outside the hospital. One problem with conventional medical telemetry systems is that patients cannot be monitored or located after they leave the coverage area.

BRIEF DESCRIPTION OF THE INVENTION

The above-mentioned shortcomings, disadvantages and problems are addressed herein which will be understood by reading and understanding the following specification.

In an embodiment, a telemetry system includes a transmitter configured to provide tracking data, and a receiver adapted to define a coverage area. The receiver is configured to receive the tracking data from the transmitter only when the transmitter is within the coverage area. The telemetry system also includes a processor configured to receive the tracking data from the receiver. The processor is configured to estimate the location of the transmitter when the transmitter is outside the coverage area based on the tracking data.

In another embodiment, a telemetry system includes a portable transmitter configured to provide tracking data, and a receiver network adapted to define a coverage area. The receiver network is configured to receive the tracking data from the portable transmitter only when the portable transmitter is within the coverage area. The telemetry system also includes a processor configured to estimate the speed of the portable transmitter based on the tracking data, estimate the trajectory of the portable transmitter based on the tracking data, and measure the elapsed time after the portable transmitter leaves the coverage area. The processor is also configured to estimate the location of the transmitter when the transmitter is outside the coverage area based on the speed of the portable transmitter, the trajectory of the portable transmitter, and the elapsed time after the portable transmitter leaves the coverage area.

In another embodiment, a method includes providing a telemetry system comprising a portable transmitter configured to provide tracking data, and a receiver network defining a coverage area. The receiver network is configured to receive the tracking data from the portable transmitter only when the portable transmitter is within the coverage area. The method also includes estimating the speed of the portable transmitter within the coverage area, estimating the trajectory of the portable transmitter within the coverage area; and measuring the elapsed time after the portable transmitter leaves the coverage area. The method also includes estimating the location of the portable transmitter based on the speed of the portable transmitter, the trajectory of the portable transmitter, and the elapsed time after the portable transmitter leaves the coverage area.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
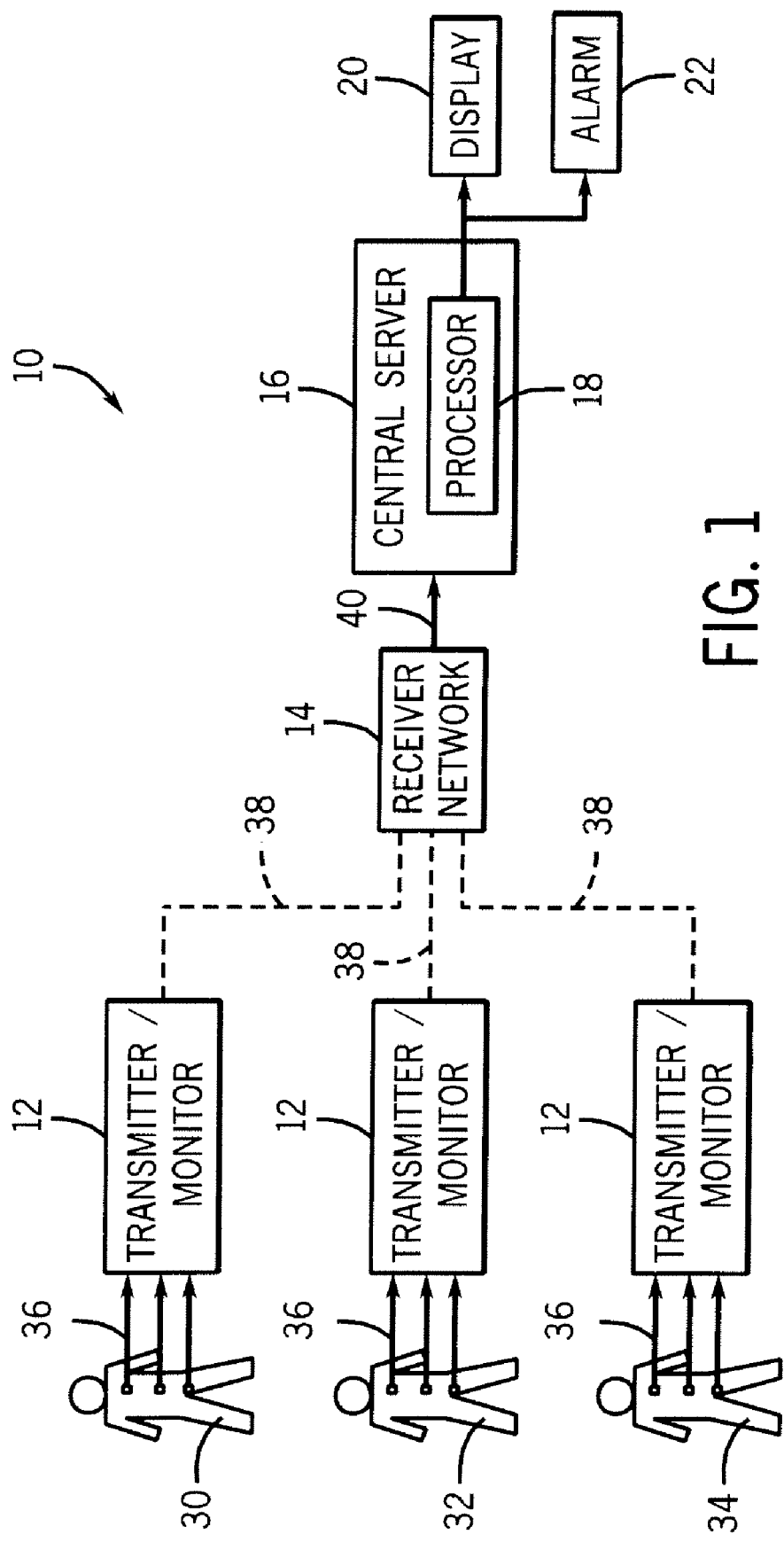
FIG. 1 is a schematic representation of a telemetry system in accordance with an embodiment.

Referring to FIG. 1, a telemetry system 10 is shown in accordance with an embodiment. The telemetry system 10 includes one or more transmitter/monitors 12; one or more receivers 14; and a central server 16 comprising a processor 18. The telemetry system 10 may also optionally include a display 20; and an alarm 22. Those skilled in the art will appreciate that the telemetry system 10 is configured to track the relative location of the transmitter/monitors 12, and that a transmitter/monitor 12 can be assigned to a specific patient in order to track and/or monitor that patient. For illustrative purposes assume that three patients 30-34 are being tracked and monitored by the telemetry system 10. It should, however, be appreciated that the telemetry system 10 may be implemented to track and/or monitor a much larger number of patients.

The transmitter/monitors 12 will be described in accordance with an embodiment as a portable device comprising an electrocardiograph and a plurality of electrograph sensors 36 configured to monitor cardiac electrical activity. For purposes of this disclosure, a portable device should be defined to include any device that is sufficiently compact and lightweight such that a typical patient can conveniently carry the device wherever they go. A separate transmitter/monitor 12 is assigned to each of the patients 30-34, and thereafter the assigned transmitter/monitor 12 generates patient monitoring data and/or patient tracking data. The patient monitoring data and/or patient tracking data from the transmitter/monitors 12 is transferred to the receivers 14 via the wireless connections 38 represented by a dashed line.

The receiver 14 will be described in accordance with an embodiment as comprising a network of receivers 14 that are uniformly distributed throughout a region of interest in order to define a coverage area. The region of interest may include a relatively small area with a high-patient density such as a patient ward. The region of interest generally does not include areas such as the cafeteria; areas with low-risk patients; areas designated exclusively for hospital staff; areas immediately outside the hospital; etc., due to economic considerations associated with the requisite infrastructure. The network of receivers 14 transfers the patient monitoring data and/or patient tracking data to the central server 16 via connection 40.

The central server 16 comprises the processor 18 configured to process the patient monitoring data and/or patient tracking data in a known manner. For example, the processor 18 may convert raw patient monitoring data acquired by the sensors 36 into more conveniently readable electrocardiogram (ECG) data comprising a P-wave, a QRS complex and a T-wave. The processor 18 may also be implemented to predict the location of a patient (or a transmitter/monitor 12 associated therewith) that has recently left a coverage area as will be described in detail hereinafter.

The display 20 may optionally be implemented to graphically convey patient monitoring data and/or patient tracking data from the central server 16 in a conveniently readable manner. As one example, the patient monitoring data may be graphically conveyed as a conventional ECG plot comprising a sequence of P-waves, a QRS complexes and a T-waves. As another example, the patient tracking data may be graphically conveyed as an icon superimposed onto a map to indicate the patient's relative location.

The alarm 22 may optionally be implemented to alert hospital personnel when a patient has exited or is about to exit a given coverage area. The alarm 22 may comprise an audible device (e.g., a loudspeaker) and/or a visual device (e.g., a flashing light). As one example, patient position may be tracked and the alarm 22 may be sounded when the patient approaches the periphery of a given coverage area. As another example, the alarm 22 may be sounded based on the patient's trajectory such that a patient walking in a direction that is generally perpendicular to the peripheral edge of a coverage area would generate an alarm while a patient walking in a direction that is generally parallel to the peripheral edge of the coverage area would not generate an alarm. As yet another example, the alarm 22 may be sounded based on the strength of a patient tracking signal from a transmitter/monitor 12 as an indication that the patient is approaching the limits of a given coverage area. As yet another example, the alarm 22 may be sounded only when the patient actually leaves a given coverage area.

Having described the components of the telemetry system 10 in detail, a method 100 (shown in FIG. 3) for predicting the location of a patient (or a transmitter/monitor 12 associated therewith) outside a coverage area will now be described with respect to FIGS. 2 and 3.

Figure 2:
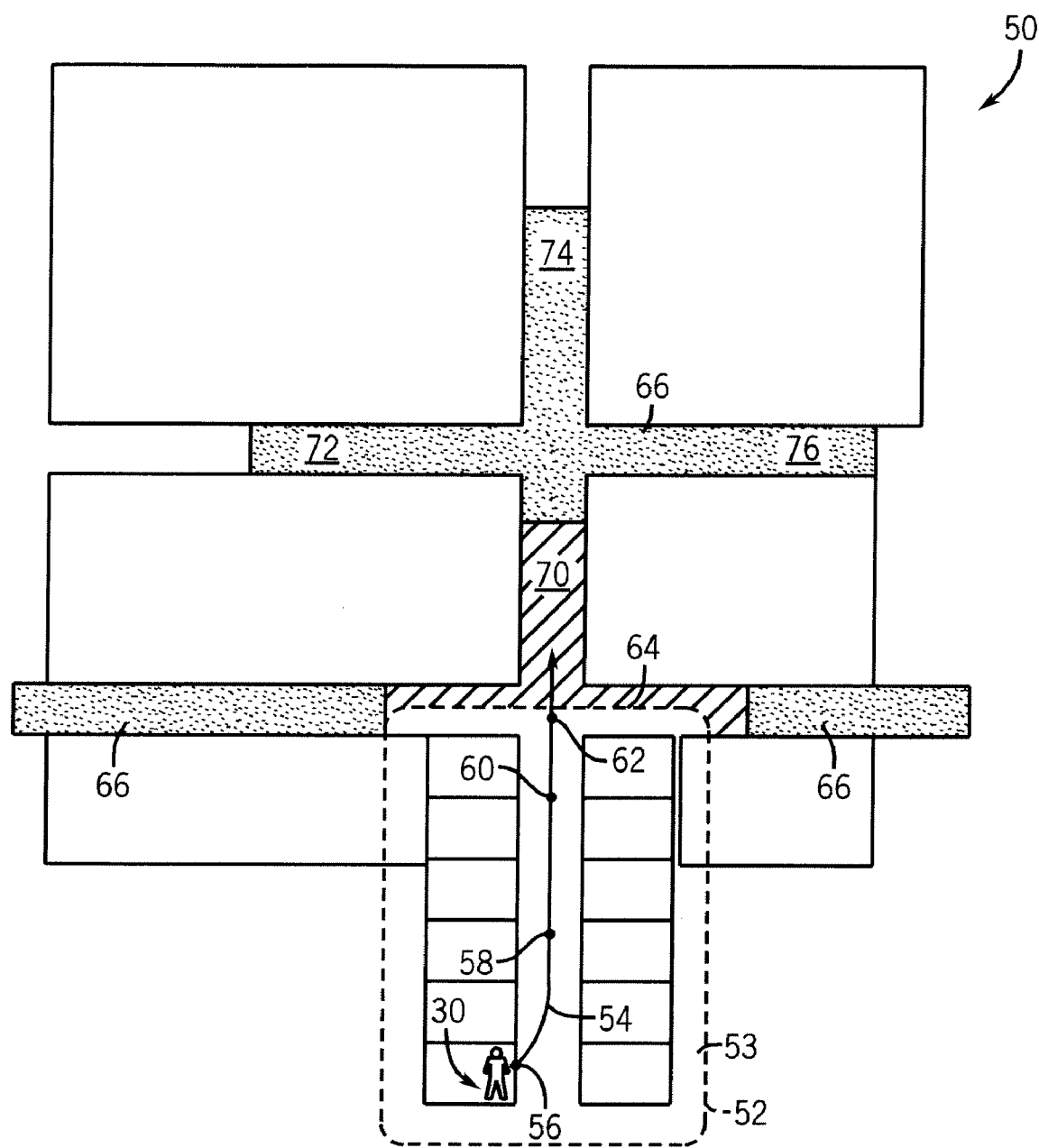
FIG. 2 is a schematic representation of a hospital map in accordance with an embodiment.

Referring to FIG. 2, a schematic representation of a hospital map 50 is shown in accordance with an embodiment. The region circumscribed by the dashed line 52 represents a coverage area 53 that may be defined by the receiver network 14 (shown in FIG. 1). As previously described, any patient having a transmitter/monitor 12 (shown in FIG. 1) can be tracked and monitored as long as they remain within the coverage area 53. As soon as a patient exits the coverage area 53, the signal from their transmitter/monitor 12 is lost and they can no longer be monitored or tracked in a conventional manner.

A solid line represents the path 54 of the patient 30 walking from a known position within the coverage area 53 to an unknown position outside the coverage area 53. Positions 56-62 are known positions along the patient's path 54 and within the coverage area 53. The cross-hatched region 64 of the map 50 represents a first region outside the coverage area 53, and the stippled region 66 of the map 50 represents a second region outside the coverage area 53. Reference numbers 70-76 identify specific hallways of the map 50.

Figure 3:
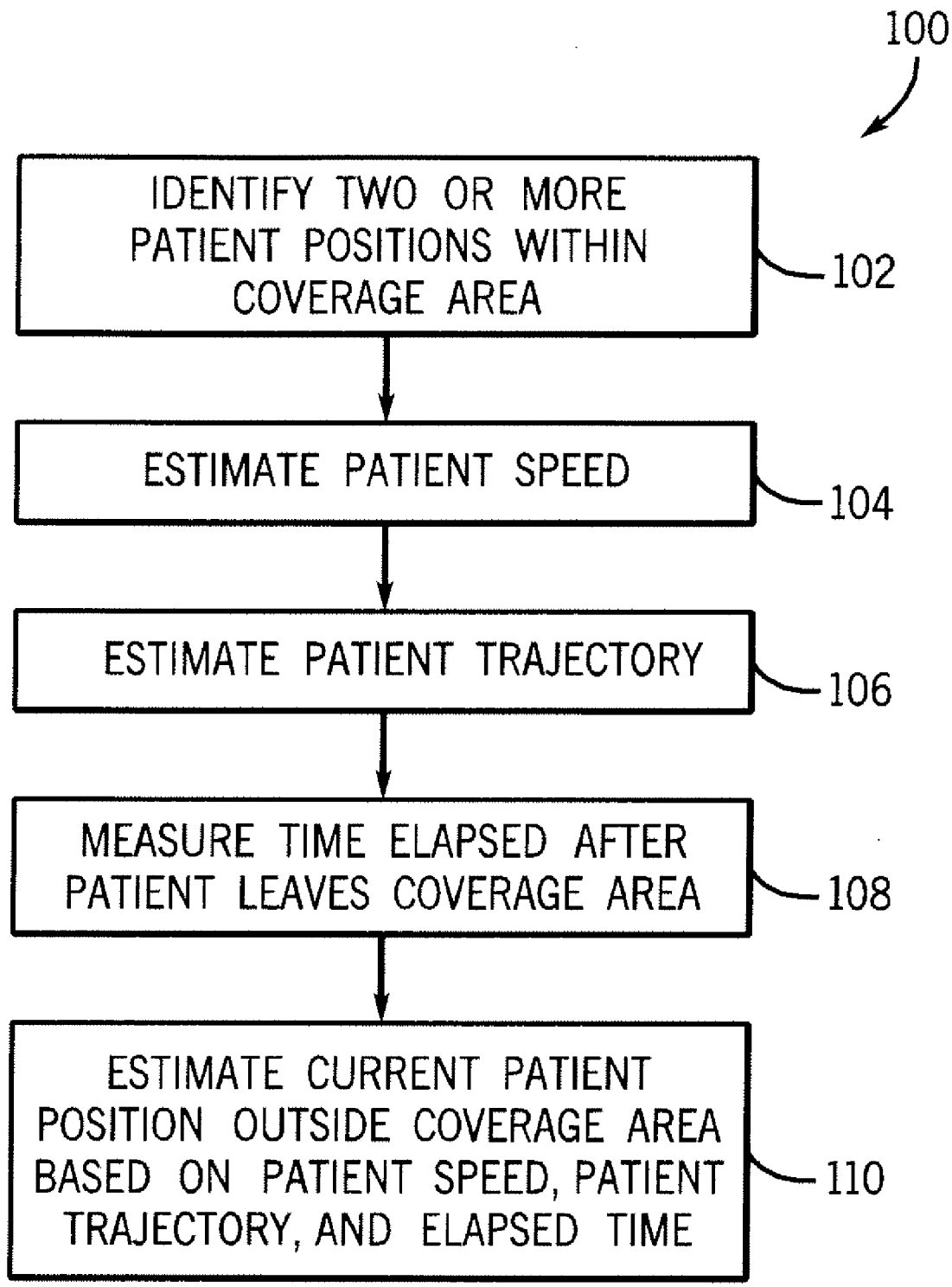
FIG. 3 is a flow chart illustrating a method in accordance with an embodiment.

Referring to FIG. 3, the method 100 for predicting the location of a patient (or a transmitter/monitor 12 associated therewith) that is disposed outside a coverage area will now be described in accordance with an embodiment. The method 100 comprises a plurality of steps 102-110. One or more of the steps 102-110 may be performed by the processor 18 (shown in FIG. 1). Referring now to both FIGS. 2 and 3, the method 100 will be described as it applies to the exemplary embodiment of FIG. 2 in order to more clearly illustrate the steps 102-110.

At step 102 the method 100 identifies two or more patient positions within the coverage area 53. For illustrative purposes, the two or more patient positions will be described as including the positions 56-62. According to one embodiment, the positions 56-62 are established by the processor 18 (shown in FIG. 1) based on patient tracking data acquired from the specific transmitter/monitor 12 (shown in FIG. 1) assigned to patient 30.

At step 104 the method 100 estimates patient speed based on the patient positions acquired at step 102. Patient speed may be estimated by the processor 18 (shown in FIG. 1) by calculating the patient's change in position divided by the change in time.

At step 106 the method 100 estimates patient trajectory based on the patient positions acquired at step 102. Patient trajectory may be estimated by the processor 18 (shown in FIG. 1) by generating a line or curve based on two or more of the positions acquired at step 102. According to one embodiment, patient trajectory may be defined by a straight line passing through both of the two most recent patient positions acquired just prior to the patient 30 leaving the coverage area 53. According to another embodiment, patient trajectory may be defined by a best-fit curve passing through three or more patient positions acquired at step 102.

At step 108 the method 100 measures the time elapsed after the patient 30 leaves the coverage area 53. At step 110 the method 100 estimates the current patient position outside the coverage area 53 based on patient speed (acquired at step 104); patient trajectory (acquired at step 106); and elapsed time (acquired at step 108).

To further illustrate step 10, assume first that only a relatively short time has passed after the patient 30 left the coverage area 53. Based on this assumption and the patient's speed (acquired at step 104), it can be estimated that the patient 30 is somewhere in the cross-hatched area 64. Additionally, based on the patient's trajectory in combination with the relatively short elapsed time, it can be estimated that the patient 30 is most likely in hallway 70.

If a relatively longer time has passed after the patient 30 left the coverage area 53, it can be estimated based on the patients speed (acquired at step 104) that the patient 30 is somewhere in the stippled area 66. Additionally, based on the patient's trajectory in combination with the relatively longer elapsed time, it can be estimated that the patient 30 is most likely in hallway 74.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:
1. A telemetry system comprising:
a transmitter configured to provide tracking data;
a receiver adapted to define a coverage area, wherein the receiver is configured to receive the tracking data from the transmitter only when the transmitter is within the coverage area; and
a processor configured to receive the tracking data from the receiver, said processor configured to estimate the location of the transmitter when the transmitter is outside the coverage area based on the tracking data received when the transmitter is within the coverage area.

2. The telemetry system of claim 1, wherein the transmitter comprises an electrocardiograph.

3. The telemetry system of claim 1, wherein the receiver comprises a network of receivers.

4. The telemetry system of claim 1, wherein the transmitter comprises a portable device assigned to a patient, and wherein the processor is configured to estimate the location of the patient based on the location of the transmitter.

5. The telemetry system of claim 4, wherein the processor is configured to estimate the speed of the patient while the patient is within the coverage area.

6. The telemetry system of claim 5, wherein the processor is configured to identify the trajectory of the patient while the patient is within the coverage area.

7. The telemetry system of claim 6, wherein the processor is configured to measure the elapsed time after the patient leaves the coverage area.

8. The telemetry system of claim 7, wherein the processor is configured to estimate the location of the transmitter based on the speed of the patient; the trajectory of the patient; and/or the elapsed time after the patient leaves the coverage area.

9. The telemetry system of claim 1, further comprising a display configured to visually convey the relative location of the transmitter.

10. The telemetry system of claim 1, further comprising an alarm configured to generate a visual and/or audible warning when the transmitter leaves or is about to leave the coverage area.

11. A telemetry system comprising:
a portable transmitter configured to provide tracking data;
a receiver network adapted to define a coverage area, wherein the receiver network is configured to receive the tracking data from the portable transmitter only when the portable transmitter is within the coverage area; and
a processor configured to estimate the speed of the portable transmitter based on the tracking data, estimate the trajectory of the portable transmitter based on the tracking data, and measure the elapsed time after the portable transmitter leaves the coverage area;
wherein the processor is configured to estimate the location of the transmitter when the transmitter is outside the coverage area based on the speed of the portable transmitter, the trajectory of the portable transmitter, and the elapsed time after the portable transmitter leaves the coverage area.

12. The telemetry system of claim 11, wherein the transmitter comprises an electrocardiograph.

13. The telemetry system of claim 11, wherein the processor is configured to estimate the location of a patient based on the location of the portable transmitter.

14. The telemetry system of claim 11, further comprising a display configured to visually convey the relative location of the portable transmitter.

15. The telemetry system of claim 11, further comprising an alarm configured to generate a visual and/or audible warning when the portable transmitter leaves or is about to leave the coverage area.

16. A method comprising: providing a telemetry system comprising:
a portable transmitter configured to provide tracking data; and
a receiver network defining a coverage area, wherein the receiver network is configured to receive the tracking data from the portable transmitter only when the portable transmitter is within the coverage area; estimating the speed of the portable transmitter within the coverage area; estimating the trajectory of the portable transmitter within the coverage area; measuring the elapsed time after the portable transmitter leaves the coverage area; and estimating the location of the portable transmitter based on the speed of the portable transmitter, the trajectory of the portable transmitter, and the elapsed time after the portable transmitter leaves the coverage area.

17. The method of claim 16, further comprising estimating the location of a patient based on the location of the portable transmitter.

18. The method of claim 16, wherein said providing a portable transmitter comprises providing a portable transmitter/monitor configured to monitor the patient.

19. The method of claim 16, further comprising generating a visual and/or audible warning when the portable transmitter leaves or is about to leave the coverage area.

* * * * *